United States Patent [19]

Noda et al.

[11] 4,395,405
[45] Jul. 26, 1983

[54] ALKYL-KETOHEXOPYRAND-SIDE DERIVATIVES AND METHOD OF USE

[75] Inventors: Kanji Noda, Chikushino; Akira Nakagawa, Tosu; Yasushi Haraguchi, Kamimine; Koichiro Ueda; Munehiko Hirano, both of Tosu; Itsuo Nishioka, Fukuoka; Akira Yagi, Kasuya; Akihide Koda, Gifu; Hiroyuki Ide, Fukuoka, all of Japan

[73] Assignee: Hisamitsu Pharmaceutical Co., Inc., Tosu, Japan

[21] Appl. No.: 150,129

[22] Filed: May 15, 1980

[30] Foreign Application Priority Data

May 23, 1979 [JP] Japan .................................. 54-64769

[51] Int. Cl.³ ...................... A61K 31/70; C07H 15/04
[52] U.S. Cl. ...................................... 424/180; 536/4.1
[58] Field of Search ...................... 536/4, 4.1; 424/180, 424/85

[56] References Cited

U.S. PATENT DOCUMENTS

| | | | |
|---|---|---|---|
| 2,715,121 | 8/1955 | Glen et al. | 536/4 |
| 2,949,449 | 8/1960 | Hoffer | 536/4 |
| 3,243,425 | 3/1966 | Whistler | 536/4 |
| 3,721,663 | 3/1973 | Hinkley et al. | 536/4 |
| 4,207,413 | 6/1980 | Szarek et al. | 536/4 |

Primary Examiner—Johnnie R. Brown
Attorney, Agent, or Firm—Jordan and Hamburg

[57] ABSTRACT

An alkyl-ketohexopyranoside derivative having pharmacological actions such as antiallergic actions, represented by the following general formula

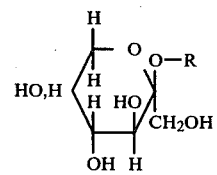

wherein R is an alkyl group having at least 3 carbon atoms, the derivatives excluding the D-fructose derivative wherein R is n-propyl group.

5 Claims, No Drawings

ALKYL-KETOHEXOPYRAND-SIDE DERIVATIVES AND METHOD OF USE

This invention relates to alkyl ketohexopyranoside derivatives represented by the following general formula

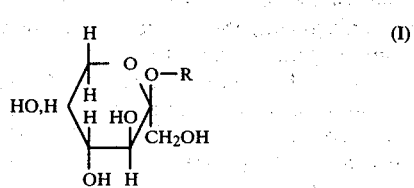

wherein R is an alkyl group containing at least three carbon atoms, the alkyl-ketohexopyranoside derivatives excluding the D-fructose derivative wherein R is n-propyl group.

The alkyl-ketohexopyranoside derivatives, the chemical compounds of this invention, are novel ones which have never been described in any literature. They have pharmacological actions such as an antiallergic action remarkably subduing allergic reactions and, therefore, they are industrially useful compounds as medicinal articles.

The symbol "R" appearing in the aforementioned general formula (I) may be n-propyl, isopropyl, n-butyl, isobutyl, n-pentyl, isopentyl, n-hexyl or isohexyl group.

In the remedy of allergic diseases, there has hitherto been used a symptomatic treatment comprising inhibiting the decomposition of tissue cells due to allergic reactions and the liberation of chemical media due thereto or comprising alleviating physiologically or symptomatically the allergic symptoms caused by the liberated chemical media. The conventionally used antiallergic medicines are mainly those for symptomatic treatment, however, it has clearly been sought from the view-point of allergic reaction mechanisms that essentially effective antiallergic medicines be developed.

In an attempt to obtain such essentially effective antiallergic medicines, the present inventors made various studies and synthesized the alkyl-ketohexopyranoside derivatives represented by the aforementioned general formula (I). After their various researches into the pharmacological actions of the alkyl-ketohexopyranoside derivatives, the present inventors have found that these derivatives are capable of selectively inhibiting the production of antibody immune globulins (IgE) causing allergic diseases without inhibiting the production of immune globulins (IgG, IgM) governing the immune reactions in normal human bodies.

Further, certain of the compounds of this invention have been found to have an action of accelerating the production of immune globulins (IgG, IgM).

More particularly, it has been found that the compounds of this invention have a remarkable essential immunity adjusting action while having no side effects which are, for example, inhibition of the production of immune globulins such as IgG, IgM or the like contained in conventional immunity inhibitors and, therefore, they are very useful as antiallergic medicines. It has also been found that certain of the compounds of this invention have capability of accelerating the production of immune globulins (IgG, IgM) and they are therefore useful as medicinal articles. This invention is based on these findings.

Now, in connection with the compounds of this invention, primafacie similar prior art compounds will be explained hereinbelow.

The compounds of this invention are clearly novel ones. Compounds having a structure similar to that of the compounds of this invention will be illustrated hereinbelow.

Journal of Food Science, Vol. 38 (1973), 665 and other like literature disclose a sorbose derivative wherein R is methyl or ethyl, the D-fructose derivative wherein R is propyl, and the like.

However, the compounds disclosed in these publications have different substituents than the compounds of this invention and the former are therefore structurally different from the latter. In addition, although the aforesaid publications only disclose that the aforesaid known compounds find their use as sweetening materials and are used only in taste tests and the like, they neither disclose nor even suggest whether or not these known compounds may be used for medicinal purposes, not to speak of the usefulness or uselessness thereof as an antiallergic or anticancer medicine.

Preparation (A)

The compounds of this invention may be obtained by the following reactions:

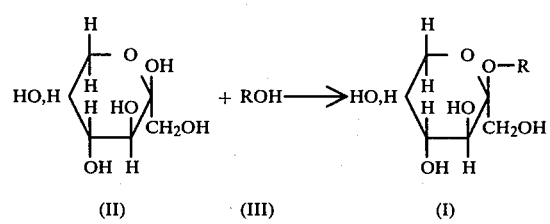

wherein R is as previously defined.

It should be noted that the formula (I) is intended to mean the following two types of compounds:

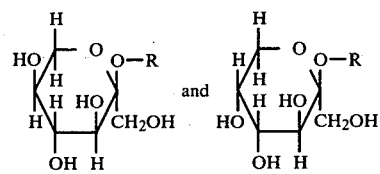

wherein R is as defined above.

The compounds of the formula (I) may be obtained by reacting a ketohexose of the formula (II) with an alcohol of the formula (III) wherein R is as defined above, in the presence of an inorganic or organic acid at room temperature or higher temperatures (preferably 20°–80° C.) for at least 0.5 hours, preferably 0.5–24 hours.

More particularly, the compounds of the formula (II) include fructose and sorbose; those of the formula (III) include lower alcohols such as n-propyl alcohol, isopropyl alcohol, n-butyl alcohol, isobutyl alcohol, sec.-butyl alcohol, n-pentyl alcohol, isopentyl alcohol, n-hexyl alcohol and isohexyl alcohol; and the acids include inorganic acids such as hydrogen chloride, sulphuric acid and phosphoric acid and also include organic acids such as formic acid, acetic acid, oxalic acid, citric acid, tartaric acid and malic acid. The reaction may be carried out at room temperature or with heating as required for preferably 0.5-24 hours. After the end of the reaction, the reaction mixture obtained is incorporated slowly with ammonia water under agitation for neutralization and the resulting precipitate is then filtered out. The filtrate so obtained is concentrated under a reduced pressure and the remaining viscous mass is freed from the unnecessary substances. The removal of the unnecessary substances is achieved, for example, by treating the remaining viscous substances with water-saturated ethyl acetate using a silica gel column or by treating the same with activated carbon or a water-alcohol mixed liquid. The unnecessary substances-freed mass is concentrated and dried under a reduced pressure to obtain a crude crystal of an alkyl-ketohexopyranoside derivative. The thus obtained crude crystal is then recrystallized from ethanol or an ethanol-ether mixed solvent thereby to obtain the end compound (I) which is a stable crystal having bitterness and no odour.

Preparation (B)

The compounds of this invention may also be obtained by the following reactions in sequence:

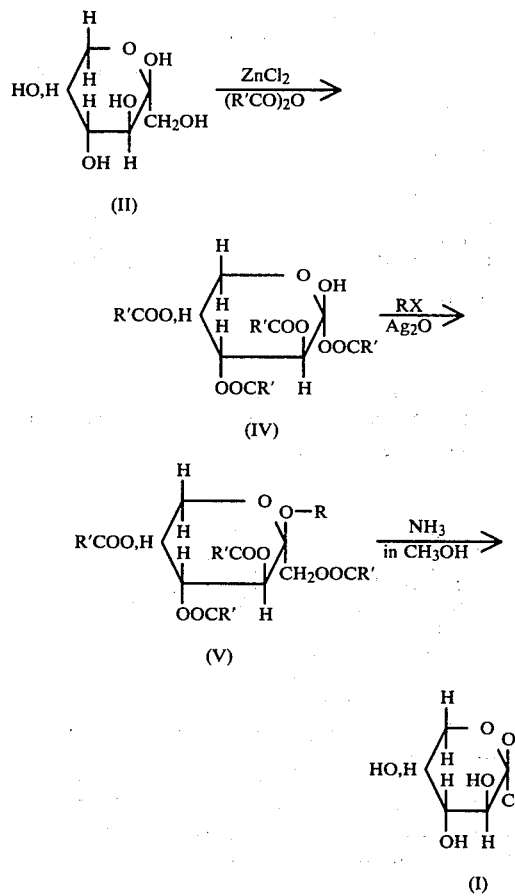

wherein R is as defined above and R' is a lower alkyl or aryl group.

More particularly, the compounds of the formula (I) may be obtained by synthesizing a compound of the general formula (IV) from a ketohexose of the formula (II), reacting the thus synthesized compound with an alkyl halide to produce a compound of the general formula (V) and then reacting the thus produced compound with ammonia gas to obtain the end compound of the formula (I). Still more particularly, the compounds of the formula (I) may be obtained by reacting fructose or sorbose of the formula (II) with zinc chloride in the presence of an acid anhydride to produce a compound of the general formula (IV), reacting the thus produced compound with an alkyl halide in the presence of silver oxide to produce a compound of the formula (V) and then reacting the thus produced compound of the formula (V) in methanol while introducing ammonia gas into the reaction system, under agitation at room temperature for 3 to 4 hours.

Further, the compounds represented by the formula (IV) may be obtained in accordance with the method described in, for example, J.A.C.S 37 2736 (1915), J.A.C.S 55 3018 (1933) and J.A.C.S 70 4052 (1948).

The end compounds of this invention are illustrated in the following Table 1.

TABLE 1

End compounds of the general formula (I-a) or (I-b)

| Compound No. | General formula | R | Melting point (°C.) | Specific rotation $[\alpha]_D$ |
|---|---|---|---|---|
| 1 | (I-a) | CH(CH$_3$)$_2$ | 112–113 | — |
| 2 | (I-a) | CH$_2$(CH$_2$)$_2$CH$_3$ | 147–149 | −138.1° |
| 3 | (I-a) | CH$_2$CH(CH$_3$)$_2$ | 157–158 | −130.0° |
| 4 | (I-a) | CH$_2$(CH$_2$)$_3$CH$_3$ | 130–131 | −123.2° |
| 5 | (I-a) | CH$_2$CH$_2$CH(CH$_3$)$_2$ | 120–122 | −131.0° |
| 6 | (I-a) | CH$_2$(CH$_2$)$_4$CH$_3$ | 130–132 | −120.0° |
| 7 | (I-b) | CH$_2$CH$_2$CH$_3$ | 94–95 | −77.3° |
| 8 | (I-b) | CH(CH$_3$)$_2$ | 98–99 | — |
| 9 | (I-b) | CH$_2$(CH$_2$)$_2$CH$_3$ | 46–47 | −73.2° |
| 10 | (I-b) | CH$_2$CH(CH$_3$)$_2$ | 79–80 | −60.2° |
| 11 | (I-b) | CH$_2$(CH$_2$)$_3$CH$_3$ | 92–93 | −70.1° |
| 12 | (I-b) | CH$_2$CH$_2$CH(CH$_3$)$_2$ | 72–73 | −65.6° |

TABLE 1-continued
End compounds of the general formula (I-a) or (I-b)

(I-a) and (I-b) structures shown with R group

| Compound No. | General formula | R | Melting point (°C.) | Specific rotation $[\alpha]_D$ |
|---|---|---|---|---|
| 13 | (I-b) | $CH_2(CH_2)_4CH_3$ | 77–78 | −77.5° |

This invention will be better understood by the following Examples wherein all the percentages are by weight unless otherwise specified.

EXAMPLE 1

410 g of n-butyl alcohol containing hydrogen chloride in an amount of 0.2% of the alcohol were incorporated with 10.0 g of D-fructose and the resulting mixture was reacted under thorough agitation at room temperature for 24 hours, after which the reaction mixture was incorporated slowly with a 25% ammonia water under agitation for neutralization. The precipitate produced was filtered out and the filtrate obtained was concentrated under a reduced pressure to obtain a viscous yellow-colored substance which was dissolved in water-saturated ethyl acetate with heating and then freed from the insoluble matters by filtration. The filtrate so obtained was concentrated and dried under a reduced pressure and the resulting dried matter was recrystallized from ethyl acetate to obtain 5.3 g of a crude crystal. The thus obtained crude crystal was then recrystallized from ethyl alcohol to obtain 3.7 g of n-butyl-$\beta$-D-fructopyranoside in the colorless needle having a melting point of 147°–149° C. and the following analysis:

Specific rotation $[\alpha]_D$: −138.1°.

Elemental analysis: Molecular formula: $C_{10}H_{20}O_6$; Calculated: C, 50.83; H, 8.53. Found: C, 50.79; H, 8.54.

EXAMPLE 2

410 g of isobutyl alcohol containing hydrogen chloride in an amount of 0.2% thereof were incorporated with 10.0 g of D-fructose and the whole mass was reacted under thorough agitation at room temperature for 24 hours, after which the reaction mixture was incorporated slowly with a 25% ammonia water to neutralize it. The precipitate produced was filtered out to obtain a filtrate which was concentrated under a reduced pressure whereby a viscous yellow-colored substance remained. The thus remaining substance was dissolved in water-saturated ethyl acetate under heat and filtered to remove the insoluble matter therefrom and obtain a filtrate. The thus obtained filtrate was concentrated and dried under a reduced pressure to obtain a dried matter which was recrystallized from ethyl acetate thereby obtaining 5.0 g of a crude crystal. The crude crystal so obtained was recrystallized from ethyl alcohol to obtain 3.5 g of isobutyl-$\beta$-D-fructopyranoside in the white needle having a melting point of 157°–158° C.

Specific rotation $[\alpha]_D$: −130.0°.

Elemental analysis: Molecular formula $C_{10}H_{20}O_6$; Calculated: C, 50.83; H, 8.53. Found: C, 50.81; H, 8.52.

EXAMPLE 3

485 g of n-pentyl alcohol containing hydrogen chloride in an amount of 0.1% thereof were incorporated with 10.0 g of D-fructose, reacted together under thorough agitation at room temperature for 24 hours and thereafter incorporated slowly with a 25% ammonia water for neutralization. The precipitate produced was filtered out and the filtrate obtained was concentrated under a reduced pressure to obtain a viscous yellow-colored substance which was dissolved in water-saturated ethyl acetate while heating and then freed from the insoluble matter by filtration. The filtrate so obtained was concentrated to dryness and recrystallized from ethyl acetate to obtain 5.2 g of a crude crystal. The thus obtained crude crystal was recrystallized from ethyl alcohol to obtain 3.5 g of n-pentyl-$\beta$-D-fructopyranoside in the colorless needle having a melting point of 130°–131° C.

Specific rotation $[\alpha]_D$: −123.2°.

Elemental analysis: Molecular formula: $C_{11}H_{22}O_6$; Calculated: C, 52.78; H, 8.86. Found: C, 52.80; H, 8.84.

EXAMPLE 4

One gram of D-fructopyranose $\beta$-1,3,4,5-tetraacetate was dissolved in 30 ml of benzene and incorporated with 2.2 g of silver oxide and 1.3 g of n-pentyl iodide. The resulting mixture was reacted under heat and reflux for 8 hours. The reaction mixture so obtained was filtered to remove the silver compound, heated under a reduced pressure to distil off the solvent, incorporated with 40 ml of methanol and allowed ammonia gas to be introduced thereinto. After the end of the reaction, the whole mass was heated under a reduced pressure to distil off the methanol, incorporated with iced water, extracted with chloroform, washed with water, dehydrated, passed into a silica gel-packed column for adsorption thereon, developed with hydrous ethyl acetate and freed from the solvent by distillation-off at the eluted portion, after which the resulting residue was recrystallized from methanol thereby to obtain 162 mg of n-pentyl-$\beta$-D-fructopyranoside in the white needle having a melting point of 130°–131° C.

Specific rotation $[\alpha]_D$: −123.2°.

Elemental analysis: Molecular formula: $C_{11}H_{22}O_6$; Calculated: C, 52.78; H, 8.86. Found: C, 52.62; H, 8.89.

EXAMPLE 5

485 g of isopentyl alcohol containing hydrogen chloride in an amount of 0.1% thereof were incorporated with 10.0 g of D-fructose and reacted under thorough agitation at room temperature for 24 hours, after which the reaction mixture was incorporated slowly with a 25% ammonia water under agitation for its neutralization and filtered to remove the produced precipitate thereby obtaining a filtrate. The filtrate so obtained was concentrated under a reduced pressure to obtain a viscous yellow-colored substance which was dissolved in water-saturated ethyl acetate while heating. The solution so obtained was filtered to remove the insoluble matter and obtain a filtrate. The thus obtained filtrate was concentrated and dried under a reduced pressure and recrystallized from ethyl acetate to obtain 4.2 g of a crude crystal. The thus obtained crude crystal was recrystallized from ethyl alcohol to obtain 2.7 g of isopentyl-β-D-fructopyranoside in the white needle having a melting point of 120°-122° C.

Specific rotation $[\alpha]_D$: −131.0°.

Elemental analysis: Molecular formula: $C_{11}H_{22}O_6$; Calculated: C, 52.78; H, 8.86. Found: C, 52.77; H, 8.87.

EXAMPLE 6

570 g of n-hexyl alcohol containing hydrogen chloride in an amount of 0.05% thereof were incorporated with 10.0 g of D-fructose to form a mixture which was reacted under thorough agitation at room temperature for 24 hours. After the end of the reaction, the resulting reaction mixture was incorporated slowly with a 25% ammonia water for neutralization. The whole mass was filtered to remove the produced precipitate and obtain a filtrate. The thus obtained filtrate was concentrated under a reduced pressure to obtain a viscous yellow-colored substance which was dissolved in water-saturated ethyl acetate with heating and filtered to remove the insoluble matter. The filtrate so obtained was concentrated and dried under a reduced pressure. The thus obtained dry matter was recrystallized from ethyl acetate to obtain 4.6 g of a crude crystal which was then recrystallized from ethyl alcohol to obtain 3.0 g of n-hexyl-β-D-fructopyranoside in the white powder crystal form having a melting point of 131°-132° C.

Specific rotation $[\alpha]_D$: −120.0°.

Elemental analysis: Molecular formula: $C_{12}H_{24}O_6$; Calculated: C, 54.53; H, 9.15. Found: C, 54.50; H, 9.16.

EXAMPLE 7

335 g of n-propyl alcohol containing sulphuric acid in an amount of 0.05% thereof were incorporated with 10.0 g of L-sorbose to form a mixture which was reacted under agitation at 70° C. for 15 hours. After cooled, the reaction mixture was incorporated with a 25% ammonia water for neutralization. The whole mass was filtered to remove the produced precipitate and obtain a filtrate. The filtrate so obtained was concentrated under a reduced pressure to obtain a viscous yellow-brown syrupy residue. The residue so obtained was dissolved in water, incorporated with activated carbon and agitated for 20-30 minutes. The whole mass was filtered to collect the activated carbon which was washed with water, incorporated with a 20% ethyl alcohol, agitated at 50° C. for 20-30 minutes to cause the desorption or elution of the adsorbed material therefrom and then filtered to obtain a filtrate. The thus obtained filtrate was concentrated and dried under a reduced pressure to obtain a light-yellow solid matter which was recrystallized from an ethyl alcohol-ether mixed solvent thereby to obtain 8.5 g of n-propyl-α-L-sorbopyranoside in the white powder crystal form having a melting point of 94°-95° C.

Specific rotation $[\alpha]_D$: −77.3°.

Elemental analysis: Molecular formula: $C_9H_{18}O_6$; Calculated: C, 48.64; H, 8.16. Found: C, 48.62; H, 8.17.

EXAMPLE 8

410 g of n-butyl alcohol containing sulphuric acid in an amount of 0.05% thereof were incorporated with 10.0 g of L-sorbose to form a mixture which was reacted under agitation at 70° C. for 15 hours. After cooled, the reaction mixture was incorporated under agitation with a 25% ammonia water for neutralization. The whole mass was filtered to remove the precipitate and obtain a filtrate. The thus obtained filtrate was concentrated under a reduced pressure to obtain a viscous yellow-brown syrupy residue. The residue so obtained was dissolved in water, incorporated with activated carbon, agitated for 20-30 minutes and filtered to recover the activated carbon. The activated carbon so recovered was washed with water and introduced into a 30% ethyl alcohol wherein it was agitated at about 50° C. for 20-30 minutes to cause the elution of the adsorbed material therefrom and then filtered to obtain a filtrate. This filtrate was concentrated and dried under a reduced pressure to obtain a light-yellow solid matter which was recrystallized from an ethyl alcohol-ether mixed solvent thereby obtaining 9.3 g of n-butyl-α-L-sorbopyranoside in the white powder crystal form having a melting point of 46°-47° C.

Specific rotation $[\alpha]_D$: −73.2°.

Elemental analysis: Molecular formula: $C_{10}H_{20}O_6$; Calculated: C, 50.83; H, 8.53. Found: C, 50.85; H, 8.54.

EXAMPLE 9

410 g of isobutyl alcohol containing sulphuric acid in an amount of 0.05% thereof were incorporated with 10.0 g of L-sorbose to form a mixture which was reacted under agitation at 70° C. for 15 hours. After cooled, the resulting reaction mixture was incorporated with a 25% ammonia water for neutralization. The whole mass was filtered to remove the produced precipitate and obtain a filtrate. The filtrate so obtained was concentrated under a reduced pressure to obtain a viscous yellow-brown syrupy residue which was dissolved in water, incorporated with activated carbon, agitated for 20-30 minutes and filtered to recover the activated carbon. The activated carbon so recovered was washed with water, introduced into a 30% ethyl alcohol, agitated in this alcohol at about 50° C. for 20-30 minutes to cause the elution of the adsorbed material from the carbon and then filtered to obtain a filtrate. This filtrate was concentrated and dried under a reduced pressure to obtain a light-yellow solid matter which was recrystallized from an ethyl alcohol-ether mixed solvent thereby obtaining 9.1 g of isobutyl-α-L-sorbopyranoside in the white powder crystal form having a melting point of 79°-80° C.

Specific rotation $[\alpha]_D$: −60.2°.

Elemental analysis: Molecular formula: $C_{10}H_{20}O_6$; Calculated: C, 50.83; H, 8.53. Found: C, 50.86; H, 8.54.

EXAMPLE 10

485 g of n-pentyl alcohol containing sulphuric acid in an amount of 0.05% thereof were incorporated with 10.0 g of L-sorbose to form a mixture which was reacted under agitation at 70° C. for 15 hours. After cooled, the resulting reaction mixture was incorporated with a 25% ammonia water for neutralization. The whole mass was filtered to remove the precipitate and obtain a filtrate. The filtrate so obtained was concentrated under a reduced pressure to obtain a viscous yellow-brown syrupy residue which was dissolved in water, incorporated with activated carbon, agitated for 20-30 minutes and filtered to recover the activated carbon. The thus recovered activated carbon was washed with water, introduced into a 30% ethyl alcohol and agitated in this alcohol at 50° C for 20-30 minutes to cause the elution of the adsorbed material from the carbon and then filtered to obtain a filtrate. This filtrate was concentrated and dried under a reduced pressure to obtain a light-yellow solid matter which was recrystallized from an ethyl alcohol-ether mixed solvent to obtain 9.2 g of n-pentyl-α-L-sorbopyranoside in the white powder crystal form having a melting point of 92°-93° C.

Specific rotation $[\alpha]_D$: −70.1°.

Elemental analysis: Molecular formula: $C_{11}H_{22}O_6$; Calculated: C, 52.78; H, 8.86. Found: C, 52.81; H, 8.85.

EXAMPLE 11

485 g of isopentyl alcohol containing sulphuric acid in an amount of 0.05% thereof were incorporated with 10.0 g of L-sorbose to form a mixture which was reacted under agitation at 70° C. for 15 hours. After cooled, the resulting reaction mixture was incorporated with a 25% ammonia water for neutralization. The whole mass was filtered to remove the produced precipitate and obtain a filtrate. The thus obtained filtrate was concentrated under a reduced pressure to obtain a viscous yellow-brown syrupy residue which was dissolved in water, incorporated with activated carbon, agitated for 20-30 minutes and filtered to recover the activated carbon. The activated carbon so recovered was washed with water, introduced into a 30% ethyl alcohol, agitated therein at about 50° C. for 20-30 minutes to cause the elution of the adsorbed material from the carbon and then filtered to obtain a filtrate. This filtrate was concentrated and dried under a reduced pressure to obtain a light-yellow solid matter which was recrystallized from an ethyl alcohol-ether mixed solvent to obtain 8.9 g of isopentyl-2-L-sorbopyranoside in the white powder crystal from having a melting point of 72°-73° C.

Specific rotation $[\alpha]_D$: −65.6°.

Elemental analysis: Molecular formula: $C_{11}H_{22}O_6$; Calculated: C, 52.78; H, 8.86. Found: C, 52.62; H, 8.89.

EXAMPLE 12

570 g of n-hexyl alcohol containing sulphuric acid in an amount of 0.05% thereof were incorporated with 10.0 g of L-sorbose to form a mixture which was reacted under agitation at 70° C. for 15 hours. After cooled, the resulting reaction mixture was incorporated under agitation with a 25% ammonia water for neutralization. The whole mass was filtered to remove the produced precipitate and obtain a filtrate. The filtrate so obtained was concentrated under a reduced pressure to obtain a viscous yellow-brown syrupy residue which was dissolved in water, incorporated with activated carbon, agitated for 20-30 minutes and filtered to recover the activated carbon. The carbon so recovered was washed with water, introduced into a 30% ethyl alcohol, agitated therein at about 50° C. for 20-30 minutes to cause the elution of the adsorbed material from the carbon and then filtered to obtain a filtrate. The filtrate so obtained was concentrated and dried under a reduced pressure to obtain a light-yellow solid matter which was recrystallized from an ethyl alcohol-ether mixed solvent thereby obtaining 8.0 g of n-hexyl-α-L-sorbopyranoside in the white powder crystal form having a melting point of 77°-78° C.

Specific rotation $[\alpha]_D$: −77.5°.

Elemental analysis: Molecular formula: $C_{12}H_{24}O_6$; Calculated: C, 54.53; H, 9.15. Found: C, 54.55; H, 9.17.

Note: In each of the Examples, the concentration at a reduced pressure was carried out at 20-30 mmHg and 60°-70° C.

The pharmacological actions of the compounds of this invention will be explained by reference to the following experiments.

EXPERIMENT 1

Effects on the formation of homocytotropic antibodies in rats

An experiment was carried out in accordance with the Tada and Okumura's method (J. Immunol., Vol. 106, p 1002, 1971).

Groups each consisting of 8-9 rats of wistar strain were used in this experiment.

As shown in Tables 2-5, to the four legs of the rats were injected 1 mg of dinitrophenylated extract of ascaris suum (DNP-As) as protein and $10^{10}$ cells of vaccinum pertussis (B. Pertussis) for sensitization, after which the compounds of this invention were administered to the injected rats for 5 days. Eight to nine days after the sensitization, bloodletting was effected on these rats to collect their serum for estimating the amount of antibodies formed using passive cutaneous anaphylaxis (PCA) reactions and phytohemaglutinin (PHA) reactions.

(1) Estimation of the amount of antibodies by PCA reaction:

The collected serum was diluted in various concentrations and intradermally injected to other rats. Forty-eight (48) hours after the injection, 2 mg of DNP-As as protein and 0.5 ml of a 1% Evans Blue were intravenously injected into these rats to determine the dilution of the serum which induced the minimum extravasted dye. The results are as shown in Tables 2 and 3. It should be noted that the symbols "*" and "**" in the following Tables indicate significant differences at risks of 5% and 1%, respectively.

TABLE 2

Effect of abdominal and oral administration on PCA of rat

| | Serum collection day | |
|---|---|---|
| | 8 days after sensitization | 9 days after sensitization |
| Test compound | Abdominal administration (100 mg/kg/day) | Oral administration (100 mg/kg/day) |
| Control | 237 (169-337) | 169 (119-223) |
| Compound No. 2 | 147 (104-208) | 84.4 (51.9-128) |
| Compound No. 3 | 73.5 (52.0-104)* | 97.0 (68.6-137) |
| Compound No. 4 | 52.0 (36.7-73.5)** | 51.9 (36.7-73.5)* |
| Compound No. 5 | — | 90.5 (64.0-128) |
| Compound No. 6 | 97.0 (64.0-147) | 147 (90.5-239) |
| Cyclophosphamide | — | 16.0 (9.19-27.8)** |

TABLE 3

Effect of hypodermic administration on PCA of rat

| Test compound | Serum collection day 8 days after sensitization | Test compound | Serum collection day 8 days after sensitization |
|---|---|---|---|
| Control | 144.5 (117.5–177.8) | Control | 269.2 (218.8–331.1) |
| Compound No. 4 | 102.4 (72.4–144.5) | Compound No. 10 | 177.8 (134.9–234.4) |
| Compound No. 7 | 67.6 (47.9–95.5) | Compound No. 11 | 154.9 (134.9–177.8)* |
| Compound No. 9 | 47.9 (36.3–83.2)* | Compound No. 12 | 234.4 (204.2–269.2) |

(2) Estimation of the amount of antibodies by PHA reaction:

The collected serum was diluted in various concentrations and incubated with sheep red blood cells coupled with DNP-As using bis-diazoated benzydine to determine the dilution of the serum which induced the minimum hemaglutination. The results are as shown in Tables 4 and 5.

TABLE 4

Effect of oral administration on PHA of rat

| Test compound | Serum collection day 8 days after the sensitization |
|---|---|
| Control | 320 (270–370) |
| Compound No. 2 | 600 (480–720)* |
| Compound No. 3 | 630 (410–840)* |
| Compound No. 4 | 3250 (900–5600)** |
| Compound No. 6 | 810 (630–990)** |

TABLE 5

Effect of hypodermic administration on PHA of rat

| Test compound | Serum collection day 8 days after sensitization | Test compound | Serum collection day 8 days after sensitization |
|---|---|---|---|
| Control | 1318.3 (933.3–1862.1) | Control | 3235.9 (2454.7–4265.8) |
| Compound No. 4 | 2454.7 (1737.8–3467.4) | Compound No. 10 | 5248.1 (3715.4–7413.1) |
| Compound No. 7 | 5248.1 (4265.8–6456.5)** | Compound No. 11 | 3467.4 (2630.3–4570.8) |
| Compound No. 9 | 5248.1 (3467.4–7943.3)* | Compound No. 12 | 6025.6 (4897.8–7413.1) |
| | | Compound No. 13 | 4265.8 (2630.3–6918.3) |

TABLE 6

Effect of oral administration on PCA of mice

| Test compound | Serum collection day | | |
|---|---|---|---|
| | 10 days after sensitization | 21 days after sensitization | 30 days after sensitization |
| Control | 256 ± 128 | 1024 ± 0 | 299 ± 43 |
| Compound No. 3 | 118 ± 37 | 563 ± 125* | 256 ± 129 |
| Compound No. 4 | 88 ± 24 | 328 ± 108** | 272 ± 80 |
| Compound No. 5 | 316 ± 86 | 480 ± 142** | 448 ± 64 |
| Compound No. 6 | 320 | 288 | 240 |
| Cyclophosphamide | 214 ± 103 | 561 ± 71** | 368 ± 146 |

TABLE 7

Effect of oral administration on PCA of mice

| Test compound | Serum collection day 10 days after sensitization |
|---|---|
| Control | 537.0 (436.5–660.7) |
| Compound No. 7 | 218.8 (109.7–436.5) |

EXPERIMENT 2

Effects on the formation of homocytotropic antibodies in mice

TABLE 8

Effect of hypodermic administration on PCA of mice

| Test compound | Serum collection day | | |
|---|---|---|---|
| | 9 days after | 10 days after | 37 days after |
| Control | 708.0 (575.4–871.0) | 537.0 (380.2–758.6) | 2818.4 (1862.1–4265.8) |
| Compound No. 7 | 660.7 (537.0–812.8) | 407.4 (288.4–575.4) | 1995.3 (1862.1–2138.0)* |
| Compound No. 9 | 708.0 (436.5–1148.2) | 218.8 (166.0–288.4) | 1513.6 (1071.5–2138.0)* |
| Compound No. 10 | 537.0 (245.5–933.3) | 708.0 (501.2–1071.5) | 1513.6 (1318.3–1737.8)** |
| Compound No. 13 | 380.2 (245.5–467.7)* | 708.0 (616.6–812.8) | 3235.9 (2630.3–3981.1) |
| Compound No. 9 | 380.2 (204.2–708.0) | | |
| Compound No. 10 | 501.2 (251.2–1000.0) | | |
| Compound No. 11 | 501.2 (1354.8–708.0) | | |
| Compound No. 12 | 269.2 (166.0–436.5) | | |

Groups each consisting of 5 female mice (BALB/c strain) were used in this experiment. The mice were sensitized with 10 μg of DNP-As as protein and 3 mg of Al(OH)$_3$, after which the test compound was administered to the sensitized mice for 5 days (at a dose of 100 mg/Kg/day). After the sensitization, a sample of serum was collected from the mice and treated in the same manner as in Experiment 1 to determine the amount of antibodies formed. The results are as shown in Tables 6–10.

TABLE 9

Effect of hypodermic administration on PCA of mice

| Test compound | Serum collection day 37 days after |
|---|---|
| Control | 3467.37 (2013.72–3767.04) |
| Compound No. 4 | 177.83 (149.62–211.35)** |
| Compound No. 9 | 251.19 (194.54–324.34)** |
| Compound No. 11 | 177.83 (140.60–224.91)** |

TABLE 10

Effect of oral administration on PHA of mice

| Test compound | Serum collection day 10 days after |
|---|---|
| Control | 125.9 (95.5–166.0) |
| Compound No. 9 | 177.8 (109.7–288.4) |
| Compound No. 10 | 109.7 (89.1–134.9) |
| Compound No. 11 | 177.8 (144.5–218.8) |
| Compound No. 12 | 109.7 (77.6–154.9) |
| Compound No. 13 | 109.7 (89.1–134.9) |

TABLE 11

Effect of hypodermic administration on PHA of mice

| Test compound | Serum collection day | | |
|---|---|---|---|
| | 9 days after | 10 days after | 37 days after |
| Control | 380.2 (269.2–537.0) | 109.7 (95.5–125.9) | 1071.5 (871.0–1318.3) |
| Compound No. 4 | 309.0 (251.2–380.2) | — | — |
| Compound No. 7 | 309.0 (251.2–380.2) | 166.0 (134.9–204.2) | 1000 (758.6–1318.3) |
| Compound No. 9 | 288.4 (245.5–354.8) | 102.3 (89.1–117.5) | 871.0 (660.7–1148.2) |
| Compound No. 10 | 154.9 (125.9–190.6) | 102.3 (83.2–125.9) | 1148.2 (933.3–1412.5) |
| Compound No. 11 | 354.8 (288.4–457.1) | 109.7 (83.2–144.5) | 1621.8 (1318.3–1995.3) |
| Compound No. 12 | 218.8 (109.7–436.5) | 144.5 (125.9–166.0) | 1230.3 (871.0–1737.8) |
| Compound No. 13 | 125.9 (83.2–190.6) | 102.3 (89.1–117.5) | 1148.2 (758.6–1737.8) |

The foregoing results indicate that IgE antibodies are detected by PCA reactions and that IgG and IgM are detected by PHA reactions. From this, it is known that the compounds of this invention will selectively inhibit the formation of IgE will not inhibit the formation of IgG and IgM. It is also known that certain of the compounds of this invention will accelerate the formation of IgG and IgM.

EXPERIMENT 3

Acute poisoning test

Each of the test compounds was suspended in a physiological solution of sodium chloride containing 0.5% of tragacanth gum to obtain a test suspension. The test suspensions so obtained were administered to rats and mice in various ways. $LD_{50}$ was calculated from test animals which died in three weeks after the start of the test. The results are as shown in Table 11 and 12.

TABLE 12

Acute poisoning test on rats

| Test compound | Manner of administration | Sex | $LD_{50}$ value (mg/Kg) |
|---|---|---|---|
| Compound No. 4 | Orally | Male | >4000 |
| | " | Female | >4000 |
| | Hypodermically | Male | 1500 (1304–1725) |
| | " | Female | 1300 (1135–1489) |
| | Abdominally | Male | >2778 |
| | " | Female | >2778 |
| | Intravenously | Male | 670 (632–710) |
| | " | Female | 660 (617–706) |
| Compound No. 7 | Orally | Male | >5000 |
| | Hypodermically | " | >5000 |
| | Abdominally | " | >5000 |
| | Intravenously | " | >2000 |
| Compound No. 10 | Orally | Male | >5000 |
| | " | Female | >5000 |
| | Hypodermically | Male | >5000 |
| | " | Female | >5000 |
| | Abdominally | Male | ≈2000 |
| | " | Female | ≈2000 |
| | Intravenously | Male | 2000> >1000 |
| | " | Female | 2000> >1000 |

TABLE 13

Acute poisoning test on mice

| Test compound | Manner of administration | Sex | $LD_{50}$ value (mg/Kg) |
|---|---|---|---|
| Compound No. 4 | Orally | Male | 3800 (3333–4332) |
| | " | Female | 3790 (3354–4283) |
| | Hypodermically | Male | 1020 (959–1085) |
| | " | Female | 1080 (1009–1156) |
| | Abdominally | Male | 2590 (2420–2771) |
| | " | Female | 2360 (2169–2568) |
| | Intravenously | Male | 760 (704–821) |
| | " | Female | 930 (857–1009) |
| Compound No. 7 | Orally | Male | >5000 |
| | Hypodermically | " | >5000 |
| | Abdominally | " | >1000 |
| | Intravenously | " | >2000 |
| Compound No. 10 | Orally | Male | 5000> >2000 |
| | " | Female | 5000> >2000 |
| | Hypodermically | Male | ≈2000 |
| | " | Female | ≈2000 |
| | Abdominally | Male | 1000> >500 |
| | " | Female | 1000> >500 |
| | Intravenously | Male | 2000> >1000 |
| | " | Female | 2000> >1000 |

As is apparent from the above results, the compounds of this invention have been confirmed to exhibit a high $LD_{50}$ value and less poisoning and have safety.

What is claimed is:

1. An antiallergic composition comprising an effective amount of an ingredient, which is a compound represented by the following general formula

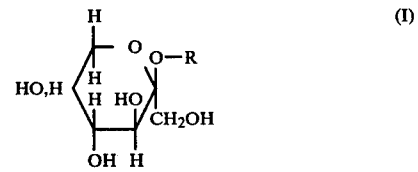

(I)

wherein R is an alkyl group having 3–6 carbon atoms, the compounds excluding the D-fructose derivatives of the α-type and D-fructose derivatives wherein R is n-propyl group, together with an inert carrier therefor.

2. A composition according to claim 1, wherein R is n-propyl, isopropyl, n-butyl, isobutyl, n-pentyl, isopentyl, n-hexyl or isohexyl group in the general formula (I).

3. The method of selectively treating the production of antibody immune globulins causing allergic diseases without inhibiting the production of immune globulins governing immune reaction by administering an antiallergic effective amount of a compound represented by the following general formula

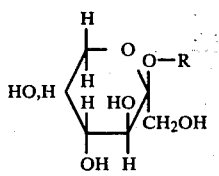 (I)

wherein R is an alkyl group having 3–6 carbon atoms, the compounds excluding the D-fructose derivative wherein R is n-propyl group.

4. An alkyl-ketohexopyranoside derivative represented by the following general formula

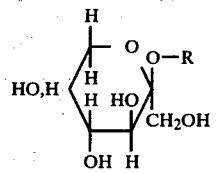 (I)

wherein R is an alkyl group having 3–6 carbon atoms, the alkyl-ketohexopyranoside derivative excluding the D-fructose derivatives of the α-type and D-fructose derivatives wherein R is an n-propyl group.

5. An alkyl-ketohexopyranoside derivative according to claim 4, wherein R is n-propyl, isopropyl, n-butyl, isobutyl, n-pentyl, isopentyl, n-hexyl or isohexyl group in the general formula (I).

* * * * *